United States Patent
Alur et al.

(10) Patent No.: US 12,303,563 B2
(45) Date of Patent: *May 20, 2025

(54) TOPICAL FORMULATIONS AND TREATMENTS

(71) Applicant: TriLogic Pharma, LLC, Tallassee, AL (US)

(72) Inventors: Hemant H. Alur, Basking Ridge, NJ (US); James A. H. Harwick, Tallassee, AL (US)

(73) Assignee: TriLogic Pharma, LLC, Tallassee, AL (US)

( * ) Notice: Subject to any disclaimer, the term of this patent is extended or adjusted under 35 U.S.C. 154(b) by 326 days.

This patent is subject to a terminal disclaimer.

(21) Appl. No.: 17/408,792

(22) Filed: Aug. 23, 2021

(65) Prior Publication Data

US 2022/0040306 A1 Feb. 10, 2022

Related U.S. Application Data

(63) Continuation of application No. 15/746,012, filed as application No. PCT/US2016/042843 on Jul. 18, 2016, now Pat. No. 11,129,896.

(60) Provisional application No. 62/194,518, filed on Jul. 20, 2015.

(51) Int. Cl.
*A61K 47/10* (2017.01)
*A61K 9/00* (2006.01)
*A61K 9/06* (2006.01)
*A61K 47/02* (2006.01)
*A61K 47/36* (2006.01)
*A61P 15/02* (2006.01)
*A61P 31/04* (2006.01)

(52) U.S. Cl.
CPC ............ *A61K 47/10* (2013.01); *A61K 9/0034* (2013.01); *A61K 9/06* (2013.01); *A61K 47/02* (2013.01); *A61K 47/36* (2013.01); *A61P 15/02* (2018.01); *A61P 31/04* (2018.01)

(58) Field of Classification Search
None
See application file for complete search history.

(56) References Cited

U.S. PATENT DOCUMENTS

| 6,218,023 | B1 | 4/2001 | DeNicola et al. |
| 6,632,796 | B1 | 10/2003 | Zeng |
| 8,691,278 | B2 | 4/2014 | Alur et al. |
| 8,709,385 | B2 | 4/2014 | Tamarkin |
| 8,883,280 | B2 | 11/2014 | Leser et al. |
| 10,011,696 | B2 | 7/2018 | Leser et al. |
| 11,129,896 | B2 | 9/2021 | Alur et al. |
| 2004/0167223 | A1 | 8/2004 | Popp |
| 2010/0105750 | A1 | 4/2010 | Aksamit et al. |
| 2018/0207275 | A1 | 7/2018 | Alur et al. |

FOREIGN PATENT DOCUMENTS

| CN | 1593386 A | 3/2005 |
| CN | 102525884 A | 7/2012 |
| WO | WO 2009/073658 A1 | 6/2009 |

OTHER PUBLICATIONS

Grant & Hackh's Chemical Dictionary (5th Ed. 1987) at p. 148.*
Extended European Search Report, for European Application No. 16828382.8 mailed Feb. 12, 2019.
International Search Report and Written Opinion, for International Application No. PCT/US2016/042843 mailed Sep. 23, 2016.
International Preliminary Report on Patentability for International Application No. PCT/US2016/042843, mailed Feb. 1, 2018.
[No Author Listed], Clindesse FDA-Approved Prescribing Information (Revision Date May 2011).
[No Author Listed], Solareze FDA-Approved Prescribing Information (Dated Dec. 2011).
[No Author Listed], Dare Bioscience Announces Positive Topline Results From DARE-BVFREE, a Phase 3 Trial of DARE-BV1 in Patients Diagnosed with Bacterial Vaginosis. Dec. 7, 2020.
Garg et al., Compendium of Pharmaceutical Excipients for Vaginal Formulations. Pharmaceutical Technology, 2001, 25, 14-24.
Jolly et al. Formulation Development and Evaluation of In Situ Gel for Vaginal Drug Delivery of Anti-Fungal Drug, Pharma Science Monitor 5(2), Sup-1, pp. 343-364, 2014; abstract; p. 347, Table 1.
Joshi et al., Formulation and Evaluation of Cefuroxime Axetil Sol Gel for Periodontits, Int J Pharm Pharm Sci, vol. 6, Issue 7, pp. 498-503, 2014.

* cited by examiner

*Primary Examiner* — Po-Chih Chen
(74) *Attorney, Agent, or Firm* — Jordan IP Law, LLC

(57) ABSTRACT

Provided is a pharmaceutical formulation and a method associated therewith for treating bacterial vaginosis. The pharmaceutical formulation includes from 10 to 25 weight parts of poloxamer F127, from 0.5 to 3.0 weight parts of xanthan gum, from 70 to 90 weight parts of water, and a therapeutically effective amount of a pharmaceutical active ingredient. The pharmaceutical formulation may also include from 0.5 to 1.5 weight parts of benzyl alcohol.

22 Claims, No Drawings

TOPICAL FORMULATIONS AND TREATMENTS

FIELD OF THE INVENTION

The present invention is in the field of treating bacterial vaginosis. The invention relates particularly to a pharmaceutical formulation for treating bacterial vaginosis.

BACKGROUND OF THE INVENTION

Bacterial vaginosis is a disease of the vagina caused by excessive bacteria. Typically, bacterial vaginosis is caused by an imbalance of the naturally occurring bacteria in the vagina. Common treatments include systemic and topical antibiotics. However, these common treatments have low clinical, nugent and therapeutic cure rates. As such, there is a need for a drug product that can effectively treat bacterial vaginosis with increased clinical, nugent and therapeutic cure rates.

U.S. Pat. No. 8,691,278 describes a bioerodible composition that serves as a drug eluting implant to prevent the entry of bacterial pathogens into periodontal pockets. The bioerodible composition includes poloxamer and xanthan gum. However, U.S. Pat. No. 8,691,278 does not discuss anything in regard to bacterial vaginosis, and does not discuss anything about using poloxamer and xanthan gum to treat bacterial vaginosis.

The aim of this work was to develop a pharmaceutical formulation that can effectively treat bacterial vaginosis with high clinical, nugent and therapeutic cure rates.

SUMMARY OF THE INVENTION

The inventors have surprisingly discovered an effective pharmaceutical formulation to treat bacterial vaginosis.

One aspect of the present invention relates to a method of treating bacterial vaginosis in a patient in need thereof. The method includes administering to the patient a pharmaceutical formulation. The pharmaceutical formulation includes (i) from 70 to 90 weight parts of water; (ii) from 10 to 25 weight parts of a copolymer having the following block structure:

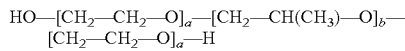

wherein the ratio of a:b is from 2:1 to 4:1, and the molecular weight of the copolymer is from 9000 to 16000; (iii) from 0.5 to 3.0 weight parts of xanthan gum; and (iv) a therapeutically effective amount of said pharmaceutical active ingredient.

Another aspect of the present invention relates to a pharmaceutical formulation for treating bacterial vaginosis in a patient in need thereof. The pharmaceutical formulation includes (i) from 70 to 90 weight parts water; (ii) from 10 to 25 weight parts of a copolymer having the following block structure:

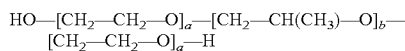

wherein the ratio of a:b is from 2:1 to 4:1, and the molecular weight of said copolymer is from 9000 to 16000; (iii) from 0.5 to 3.0 weight parts of xanthan gum; (iv) from 0.5 to 1.5 weight parts of benzyl alcohol; and (v) a therapeutically effective amount of a pharmaceutical active ingredient.

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

Definitions and Use of Terms

As used in this specification and in the claims, which follow, the singular forms "a," "an" and "the" include plural referents unless the context clearly dictates otherwise. Thus, for example, reference to "an ingredient" includes mixtures of ingredients; reference to "an active pharmaceutical agent" includes more than one active pharmaceutical agent, and the like.

"Pharmaceutically acceptable" means that which is useful in preparing a pharmaceutical composition that is generally safe, non-toxic and neither biologically nor otherwise undesirable and includes that which is acceptable for human pharmaceutical use.

"Therapeutically effective amount" means that amount which, when administered to an animal for treating or preventing a disease, is sufficient to effect such treatment or prevention for the disease.

When ranges are given by specifying the lower end of a range separately from the upper end of the range, it will be understood that the range can be defined by selectively combining any one of the lower end variables with any one of the upper end variables that is mathematically possible.

When used herein the term "about" or "ca." will compensate for variability allowed for in the pharmaceutical industry and inherent in pharmaceutical products, such as differences in product strength due to manufacturing variation and time-induced product degradation. The term allows for any variation, which in the practice of pharmaceuticals would allow the product being evaluated to be considered bioequivalent in humans to the recited strength of a claimed product.

Discussion

The present invention relates to a pharmaceutical formulation for treating bacterial vaginosis. The pharmaceutical formulation may include an active ingredient, one or more excipients, and water. In one example, the active ingredient may include clindamycin phosphate. The excipients may include one or more of the following: poloxamer, xanthan gum, a preservative such as benzyl alcohol, and a pH buffer such as a citrate buffer.

The term "poloxamer" refers to any of the group of polyoxyethylene-polyoxypropylene block copolymers known in the art. Poloxamers are also known by the trade names Pluronics™ and Lutrol™ and are nonionic block copolymers composed of a central hydrophobic chain of polyoxypropylene (polypropylene oxide) flanked by two hydrophilic chains of polyoxyethylene (polyethylene oxide). Because the lengths of the polymer blocks can be customized, many different poloxamers exist that have slightly different properties.

Poloxamers may be soluble in water and other polar and non-polar solvents and are regarded as chemically inert. Commercially, poloxamers may be available from BASF as flakes (denoted by "F"), paste (denoted by "P"), liquid (denoted by "L") and micronized (denoted by "micro").

The pharmaceutical formulation of the present invention may be based upon poloxamers having an ethylene oxide/n-propylene oxide block polymer structure, random or ordered. The ethylene oxide preferably may be in molar excess to the n-propyl oxide, and the ratio of ethylene oxide to n-propyl oxide units (i.e. a:b) may be from 2:1 to 4:1. In one embodiment the block copolymer has the following block polymer structure:

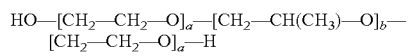

The structure consists of a hydrophobic central core of propylene oxide (represented by "b" in the above FIGURE), flanked by hydrophilic ethylene oxide (represented by "a" in the above FIGURE) on both sides. The molecular weight of the copolymer may be in one embodiment from 5000 to 25000. In some instances, the molecular weight of the copolymer may be from 9000 to 16000. The sum of the two a's preferably is from 50 to 500, from 100 to 300, from 150 to 250, or 200. b is preferably from 30 to 100, from 50 to 80, from 60 to 70, or 65. The ratio of the 2 a's to b is preferably from 2:1 to 4:1.

In one embodiment, the poloxamer used in the pharmaceutical formulation of the present invention is poloxamer F127. In Poloxamer F127, the sum of two a's in the above block polymer structure may be 200, and b may have a value of 65. In Poloxamer F127, the ratio of the sum of two a's to b in the poloxamer (i.e. a:b) may be from 2:1 to 4:1. Tables 1 and 2 illustrate chemical composition and specifications of Poloxamer F127.

modulated by varying the percentage of F127, or mixing it with one or more other poloxamers.

Xanthan gum refers to a high molecular weight polysaccharide used as a food additive and rheology modifier. It may be produced by a process involving fermentation of glucose or sucrose by the *Xanthomonas campestris* bacterium. The backbone of the polysaccharide chain consists of two β-D-glucose units linked through the 1 and 4 positions. The side chain consists of two mannose and one glucuronic acid, so the chain consists of repeating modules of five sugar units. The side chain is linked to every other glucose of the backbone at the 3 position. About half of the terminal mannose units have a pyruvic acid group linked as a ketal to its 4 and 6 positions. The other mannose unit has an acetyl group at the 6 positions. Two of these chains may be aligned to form a double helix, giving a rather rigid rod configuration that accounts for its high efficiency as a viscosifier of water. The molecular weight of xanthan varies from about one million to 50 million depending upon how it is prepared. In a preferred embodiment for the current invention, the molecular weight of the xanthan ranges from approximately 1 to 25 million, as measured by a Brookfield Viscometer. In alternative embodiments, the molecular weight is 1, 2, 3, 4, or 5±0.5, or 6, 7, 8, 9, 10, 11, 12, 13, 14, 15, 16, 17, 18, 19, 19, 20, 21, 22, 23, 24, or 25±2.

In one embodiment, the pharmaceutical formulation of the present invention may include from 10 to 25 weight parts of the poloxamer. In some instances, the pharmaceutical formulation may include from 10 to 20 weight parts of the poloxamer.

In one embodiment, the pharmaceutical formulation of the present invention may include from 0.50 to 3.0 weight

TABLE 1

Chemical Composition of Poloxamer F127

| Pluronic ® | Poloxamer | a | b | Content of Oxyethylene (Percent) | Molecular Weight | Number average molecular weight (g/mol) | Polydispersity index | Number of repeating units |
|---|---|---|---|---|---|---|---|---|
| F 127 NF | 407 | 101 | 56 | 71.5-74.9 | 9840-14600 | 10000 | 1.2 | $EG_{200}PG_{65}PH_0$ |

TABLE 2

Specifications of Poloxamer F127

| Physical Form | pH (2.5% in water) | Cloud point, 10% | APHA color | % H₂O | BHT, ppm | Unsaturation mEq/g | Ethylene Oxide, ppm | Propylene Oxide, ppm | 1,4 dioxane, ppm |
|---|---|---|---|---|---|---|---|---|---|
| Solid | 5.0-7.5 | >100° C. | 120 max. | Cast solid 0.4 max. Prill 0.75 max. | 50-125 | 0.048 ± 0.017 | 1 max. | 5 max. | 0.002% max. |

Poloxamers show temperature dependent thermoreversible properties. Poloxamer F127 is the most well studied poloxamer for this behavior. Generally, this behavior has been studied in 20-30% w/w aqueous solutions, which are liquid at low temperature (2-5° C.) and turn into a gel at room temperature (22-25° C.). This gelation temperature is dependent on the molecular weight and the percentage of the hydrophobic portion, hence the gelling temperature decreases as both the molecular weight and the hydrophobic fraction increases. The gelation temperature can also be parts of xanthan gum. In some instances, the pharmaceutical formulation may include from 1.5 to 2.5 weight parts of xanthan gum. Higher weight parts of xanthan gum may also be used, but may likely result in a product with high viscosity, which may be difficult to handle.

In one embodiment, the pharmaceutical formulation may include from 70 to 90 weight parts of water. In some instances, the pharmaceutical formulation may include from 75 to 85 weight parts of water.

In one embodiment, the pharmaceutical formulation may include 1.5 to 3.5 or 4.0, preferably 2.0, weight parts of the pharmaceutical active ingredient, such as clindamycin or a pharmaceutically acceptable salt thereof (e.g. clindamycin phosphate), wherein the weight of the clindamycin is based on the weight of the free base. Other suitable antibiotics include metronidazole, clotrimazole, secnidazole, ornidazole, tinidazole, probiotics and boric acid.

In one embodiment, the pharmaceutical formulation may include one or more conventional pharmaceutical excipients selected from stabilizers, antioxidants, preservatives, buffers and pH regulating agents.

In one embodiment, the pharmaceutical formulation may include from 0.5 to 1.5 weight parts of benzyl alcohol. A preferred buffer is a citrate buffer and it is preferably present in the formulation in a concentration of from 0 to 100 mM, 25-100 nM, or approximately 50 mM.

In one embodiment the pharmaceutical formulation includes from 0.1 to 1.0 weight parts of citric acid and from 0.5 to 2.5 weight parts of sodium citrate, or other suitable salts to make citrate buffer such as sodium phosphate, potassium phosphate.

The tables below illustrate two examples of pharmaceutical formulation of the present invention. The tables below are purely exemplary of the invention and are not intended to limit the scope of what the inventors regard as their invention. Unless indicated otherwise, parts are parts by weight. The weight parts 2.44% illustrated in Table 3 (refers to the weight of clindamycin phosphate that is equivalent to 2% of clindamycin base) may simply refer to that of Clindamycin, not phosphate (PO4).

TABLE 3a

Example Pharmaceutical Formulation

| Raw material | % (w/w) |
|---|---|
| Poloxamer F127, USP | 16.50 |
| Xanthan gum, USP | 2.00 |
| Clindamycin PO4, USP* | 2.44 |
| Citric acid monohydrate, USP | 0.39 |
| Sod. Citrate anhydrous, USP | 0.82 |
| Benzyl alcohol, USP | 1.00 |
| Purified Water, USP qs | 76.85 |
| Total | 100.00 |

*equivalent to 2% clindamycin

TABLE 3b

Example Pharmaceutical Formulation

| Raw material | % (w/w) |
|---|---|
| Poloxamer F127, USP | 16.50 |
| Xanthan gum, USP | 2.00 |
| Clindamycin PO4, USP* | 2.44 |
| Citric acid anhydrous, USP | 0.60 |
| Sod. Citrate dihydrate, USP | 0.55 |
| Benzyl alcohol, USP | 1.00 |
| Purified Water, USP qs | 76.91 |
| Total | 100.00 |

* equivalent to 2% clindamycin

The pharmaceutical formulation of the present invention may also be defined by several chemical characteristics, including a gel temperature that is between room temperature and the body temperature of a patient, e.g., 37° C. The pharmaceutical formulation in one embodiment may have a viscosity at room temperature of from 100,000 to 1,000,000 cps. In another embodiment, the viscosity of the pharmaceutical formulation may range from 200,000 to 500,000 cps. In addition, the pharmaceutical formulation may include no component other than the above described that may change the viscosity of the pharmaceutical formulation at room temperature (i.e. by more than 100,000, 50,000 or 10,000 cps).

The pharmaceutical formulation may also include an antibiotic. A therapeutically effective amount of the antibiotic may be released from 1 to 21 days. In some instances, a therapeutically effective amount of the antibiotic may be released up to about 5 or 15 days following administration.

The pharmaceutical formulation may be free or mass flowing, so that it may be administered through an applicator or other suitable device.

Trials Conducted

Two trials were conducted to test the efficacy and safety of the pharmaceutical formulation of the present invention in the treatment of bacterial vaginosis. The first study focused on Amsel criteria (clinical cure) and the second study evaluated both Amsel criteria and Nugent (microbiological cure) scores. These multi-center proof of principle studies enrolled a total of 30 patients (20 in the first study and 10 in the second study) with confirmed cases of bacterial vaginosis. The trial was conducted in accordance with the 1998 draft guidance document published by FDA (Bacterial Vaginosis—Developing Antimicrobial Drugs for Treatment).

The subjects of the trial included females 18 years of age and older with a confirmed clinical diagnosis of bacterial vaginosis. Each female was administered a single dose of a pharmaceutical formulation of the present invention. Clinical and microbiological evaluations were performed as detailed in the guidance document at baseline, post-treatment and test of cure visits.

At baseline visit (day 1), patient information was gathered and a pelvic examination was performed to establish eligibility. If all study requirements were met and patient consented for enrollment and adhering to study protocol, a single dose treatment of the pharmaceutical formulation of the present invention was provided. The following tests were performed; (a) physiological symptoms such as discharge and odor, (b) pH, (c) saline "wet mount" to check for the presence of clue cells, (d) 10% KOH "whiff test" and (e) urine pregnancy (if necessary). In addition, in the second study, a microscopic evaluation of the vaginal smear was performed and scored as per Nugent method. The Nugent scoring was based on microscopic examination of the Gram's stained vaginal smears for quantification of specific bacterial morphotypes.

At post-treatment visit (day 8 to day 15), patients were questioned about the comfort level after the initial treatment and then re-examined. Following pelvic examination, the above-mentioned tests were repeated.

At test-of-cure visit (day 22 to day 29), patients were questioned about their experience and following pelvic examination the above-mentioned tests were repeated.

The primary efficacy endpoint in the first study was the clinical cure, which includes the clinical response of the subject at the test-of-cure visit (Visit 3) and in the second study both clinical and therapeutic cure were evaluated.

Clinical cure was defined as resolution of the clinical findings from the baseline visit. Subjects may have all of the following:

The original discharge characteristic of bacterial vaginosis has returned to a normal physiological discharge.

The 10% KOH "whiff test" is negative.

The saline wet mount is negative for clue cells.

The vaginal fluid pH is <4.7.

Therapeutic cure was a composite endpoint, which required both clinical cure (as defined above) and Nugent score cure. A Nugent score of 0-3 was considered a Nugent score cure.

To evaluate safety, subjects were questioned about their comfort level and any adverse reactions they experienced after receiving the pharmaceutical formulation of the present invention.

Twenty (20) patients between the ages of 18 and 50 enrolled for the first study. Of the 20 subjects, 2 subjects did not complete the study (one voluntarily opted for oral medication for odor after 1$^{st}$ week in spite of negative outcomes and one did not attend the second appointment) and 1 subject was treated orally after 1$^{st}$ week due to menses. Therefore, these 3 subjects were excluded from cure rate calculations.

Ten (10) patients between the ages of 18 and 50 enrolled for the second study. Of the 10 subjects, 1 subject was excluded from the study for positive STD test. Therefore, this subject was excluded from cure rate calculations.

At post-treatment visit (day 8 to day 15), subjects reported no adverse reactions or uncomfortable feeling after receiving the pharmaceutical formulation of the present invention. There were 2 subjects in the first study, who received a second dose of the pharmaceutical formulation of the present invention during the post-treatment visit and were excluded from cure rate calculations.

At test-of-cure visit (day 22 to day 29), between the two studies, 24 subjects successfully completed the study course. At the test-of-cure visit, 20 of 24 subjects (87%) were successfully treated (clinical cure) with one dose of the pharmaceutical formulation of the present invention.

1 of the 2 subjects receiving the second dose at post-treatment visit was successfully treated (clinical cure).

Of the 24 subjects completing the study, 9 were evaluated for Nugent cure. At the test-of-cure visit, 7 of 9 subjects (78%) were successfully treated (Nugent cure) with one dose of the pharmaceutical formulation of the present invention.

No adverse reactions were reported by the subjects during this phase.

Subjects' comfort level and acceptance of the pharmaceutical formulation of the present invention were very high throughout the study. No adverse reactions were reported during the entire study period.

Table 4 below illustrates efficacy of the pharmaceutical formulation of the present invention in comparison with other known drugs for treating bacterial vaginosis.

TABLE 4

Efficacy of drugs for the Treatment of
Bacterial Vaginosis in Multi-center PoP Studies

| Product | Clinical Cure | Nugent Cure | Therapeutic Cure |
|---|---|---|---|
| Pharmaceutical formulation of the present invention | 87% | 78% | 67%$^a$ |
| Clindesse ®$^b$ | 41% | 45% | 30% |
| Metronidazole vaginal gel, 1.3%$^c$ | 37% | 20% | 17% |

$^a$based on the second study with 9 evaluable patients.
$^b$www.clindesse.com/pdf/PI.pdf
$^c$www.accessdata.fda.gov/drugsatfda_docs/label/2014/205223s0001b1.pdf As show in Table 4, the pharmaceutical formulation of the present invention is showing a trend of high clinical and Nugent cure rates with just one dose compared to other approved single dose products. This coupled with clindamycin's proven bacteriological efficacy in humans may translate to a better treatment option as well. The data obtained thus far from these small clinical trials show that a single dose of the pharmaceutical formulation of the present invention is beneficial in treating bacterial vaginosis and providing comfort from related symptoms.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A pharmaceutical formulation, comprising:
    (i) from 70 to 90 weight parts of water;
    (ii) from 10 to 25 parts of a copolymer having the following block structure:

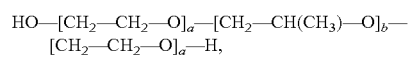
    $$HO-[CH_2-CH_2-O]_a-[CH_2-CH(CH_3)-O]_b-[CH_2-CH_2-O]_a-H,$$

wherein ratio of a:b is from 2:1 to 4:1 and, when a and b are summed, molecular weight of said copolymer is from 9000 to 16000;
    (iii) from 1.5 to 4.0 weight parts of clindamycin or a pharmaceutically acceptable salt thereof, and
    (iv) from 0.5 to 3.0 weight parts of xanthan gum, wherein the formulation is a gel and has a viscosity at room temperature of from 100,000 to 1,000,000 cps.

2. The formulation of claim 1, wherein the clindamycin or pharmaceutically acceptable salt thereof is clindamycin.

3. The formulation of claim 1, wherein the clindamycin or pharmaceutically acceptable salt thereof is clindamycin phosphate.

4. The formulation of claim 1, wherein the gel has a gel temperature that is between room temperature (22° C. to 25° C.) and body temperature.

5. The formulation of claim 1, wherein the formulation has from 1.5 to 2.5 weight parts of xanthan gum.

6. The formulation of claim 1, wherein a sum of a's in the block structure of the copolymer equals 200, and b in the block structure has a value of 65.

7. The formulation of claim 1, wherein the pharmaceutical formulation contains no other component that changes the viscosity of said formulation at room temperature by more than 100,000 centipoise.

8. The formulation of claim 1, wherein the pharmaceutical formulation further includes from 0.5 to 1.5 weight parts of benzyl alcohol.

9. The formulation of claim 1, wherein the pharmaceutical formulation further includes from 25 to 100 mM of a citrate buffer.

10. The formulation of claim 1, wherein the pharmaceutical formulation includes from 10 to 20 weight parts of said copolymer.

11. A pharmaceutical formulation, consisting essentially of:
- (i) from 70 to 90 weight parts of water;
- (ii) from 10 to 25 parts of a copolymer having the following block structure:

$$HO—[CH_2—CH_2—O]_a—[CH_2—CH(CH_3)—O]_b—[CH_2—CH_2—O]_a—H,$$

wherein ratio of a:b is from 2:1 to 4:1 and, when a and b are summed, molecular weight of said copolymer is from 9000 to 16000;
- (iii) from 0.5 to 3.0 weight parts of xanthan gum; and
- (iv) from 1.5 to 4.0 weight parts of clindamycin or a pharmaceutically acceptable salt thereof;

wherein the formulation is a gel.

12. The formulation of claim 11, wherein the clindamycin or pharmaceutically acceptable salt thereof is clindamycin.

13. The formulation of claim 11, wherein the clindamycin or pharmaceutically acceptable salt thereof is clindamycin phosphate.

14. The formulation of claim 11, wherein the formulation has a viscosity at room temperature of from 100,000 to 1,000,000 cps.

15. The formulation of claim 11, wherein the formulation is a gel having a gel temperature that is between room temperature (22° C. to 25° C.) and body temperature.

16. The formulation of claim 11, wherein the formulation has from 1.5 to 2.5 weight parts of xanthan gum.

17. A gel, comprising:
- (i) from 70 to 90 weight parts of water;
- (ii) from 10 to 25 parts of a copolymer having the following block structure:

$$HO—[CH_2—CH_2—O]_a—[CH_2—CH(CH_3)—O]_b—[CH_2—CH_2—O]_a—H,$$

wherein ratio of a:b is from 2:1 to 4:1 and, when a and b are summed, molecular weight of said copolymer is from 9000 to 16000;
- (iii) from 0.5 to 3.0 weight parts of xanthan gum; and
- (iv) from 1.5 to 4.0 weight parts of clindamycin or a pharmaceutically acceptable salt thereof.

18. The gel of claim 17, wherein the clindamycin or pharmaceutically acceptable salt thereof is clindamycin.

19. The gel of claim 17, wherein the clindamycin or pharmaceutically acceptable salt thereof is clindamycin phosphate.

20. The gel of claim 17, wherein the gel has a viscosity at room temperature of from 100,000 to 1,000,000 cps.

21. The gel of claim 17, wherein the formulation has a gel temperature that is between room temperature (22° C. to 25° C.) and body temperature.

22. The gel of claim 17, wherein the formulation has from 1.5 to 2.5 weight parts of xanthan gum.

* * * * *